US00PP36680P2

(12) United States Plant Patent
Hansen

(10) Patent No.: US PP36,680 P2
(45) Date of Patent: May 13, 2025

(54) ***DICENTRA* PLANT NAMED 'White Diamonds'**

(50) Latin Name: ***Dicentra* hybrid**
Varietal Denomination: White Diamonds

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 18/831,339

(22) Filed: Nov. 22, 2024

(51) Int. Cl.
*A01H 5/02* (2018.01)
*A01H 6/64* (2018.01)

(52) U.S. Cl.
USPC ..... Plt./426
CPC ..... *A01H 6/64* (2018.05)

(58) Field of Classification Search
USPC ..... Plt./426
CPC ..... A01H 5/02
See application file for complete search history.

*Primary Examiner* — Kent L Bell

(57) ABSTRACT

A new and unique Fern-leafed Bleeding Heart, *Dicentra* plant named 'White Diamonds' characterized by compact habit and finely-textured, fern-like, blue-green foliage. The plant flowers with cream-colored buds that open to white, heart-shaped, lightly-fragrant flowers on panicles that have extended flowering periods on older panicles and new with panicles to stay in bloom 16 to 20 weeks beginning late spring. The new plant has an excellent growth rate.

2 Drawing Sheets

Botanical classification: *Dicentra* hybrid.
Variety denomination: 'White Diamonds'.

STATEMENT REGARDING PRIOR DISCLOSURES UNDER 37 CFR 1.77(b)(6)

The first offer for sale of the claimed plant was by Walters Gardens, Inc. to W. Altee Burpee & Co. on Dec. 1, 2023. The plant was also featured with a photo and brief description on Dec. 1, 2023, on a website maintained by Walters Gardens, Inc. and in the "Walters Gardens 2024-2025 Catalog" first released on May 23, 2024. The plants and all information for the photographs and information were obtained from the inventor. No plants of *Dicentra* 'White Diamonds' have been sold or offered for sale in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct *Dicentra* 'White Diamonds' hereinafter referred to also by the cultivar name 'White Diamonds' and the new plant. 'White Diamonds' is the result of a cross between *Dicentra* 'Ivory Hearts' U.S. Plant Pat. No. 15,599 as the female and *Dicentra peregrina* x *eximia* hybrid 'Red Fountain' U.S. Plant Pat. No. 21,269 on Jun. 15, 2016, at a research garden at a wholesale perennial nursery in Zeeland, Michigan, USA.

Through trials at a wholesale perennial nursery the plant was referred to by the code 16-1-3. The new plant has been successfully asexually propagated initially by division since 2018 followed by shoot tip tissue culture at the same nursery in Zeeland, Michigan. Both of these asexual propagation systems has been found to produce stable and identical plants that maintain all the unique characteristics of the original plant in successive generations.

BRIEF DESCRIPTION OF THE INVENTION

The most closely known cultivars to the inventor include: 'Aurora' (not patented), 'Amore Titanium' U.S. Plant Pat. No. 35,856, and 'Ivory Hearts'.

'Aurora' has less dissected foliage. 'Amore Titanium' has peduncles with fewer flowers that remain more upright with age.

The female parent, 'Ivory Hearts', has a slightly smaller habit with shorter inflorescences flowering with fewer flowers per stem for a shorter period only in the spring. The male parent, 'Red Fountain', has dark burgundy flowers and a slightly smaller habit. Both of the parents are shorter lived in the landscape in Michigan.

The new plant, 'White Diamonds', is unique from all Fern-leaf Bleeding Hearts known to the inventor by the following combined traits:

1. Compact habit of finely-textured, fern-like blue-green foliage;
2. Creamy buds open to white, heart-shaped, lightly-fragrant flowers;
3. Repeat flowering panicles and extended flowering on older panicles;
4. Flowering beginning in late spring and continuing for 16 to 20 weeks.

BRIEF DESCRIPTION OF THE DRAWINGS

The color drawings illustrate the overall characteristics of the new plant and demonstrates the overall appearance of the new plant including the unique traits as a three-year-old plant growing in a full-sun trial garden in Zeeland, Michigan with supplemental water and fertilizer as needed. The colors are as true as reasonably possible given the technology available. The colors are as accurate as reasonably possible with color reproductions. Ambient light, spectrum, temperature, source, duration and direction may cause minor variation in appearance.

DETAILED DESCRIPTION OF THE INVENTION

Figure 1:
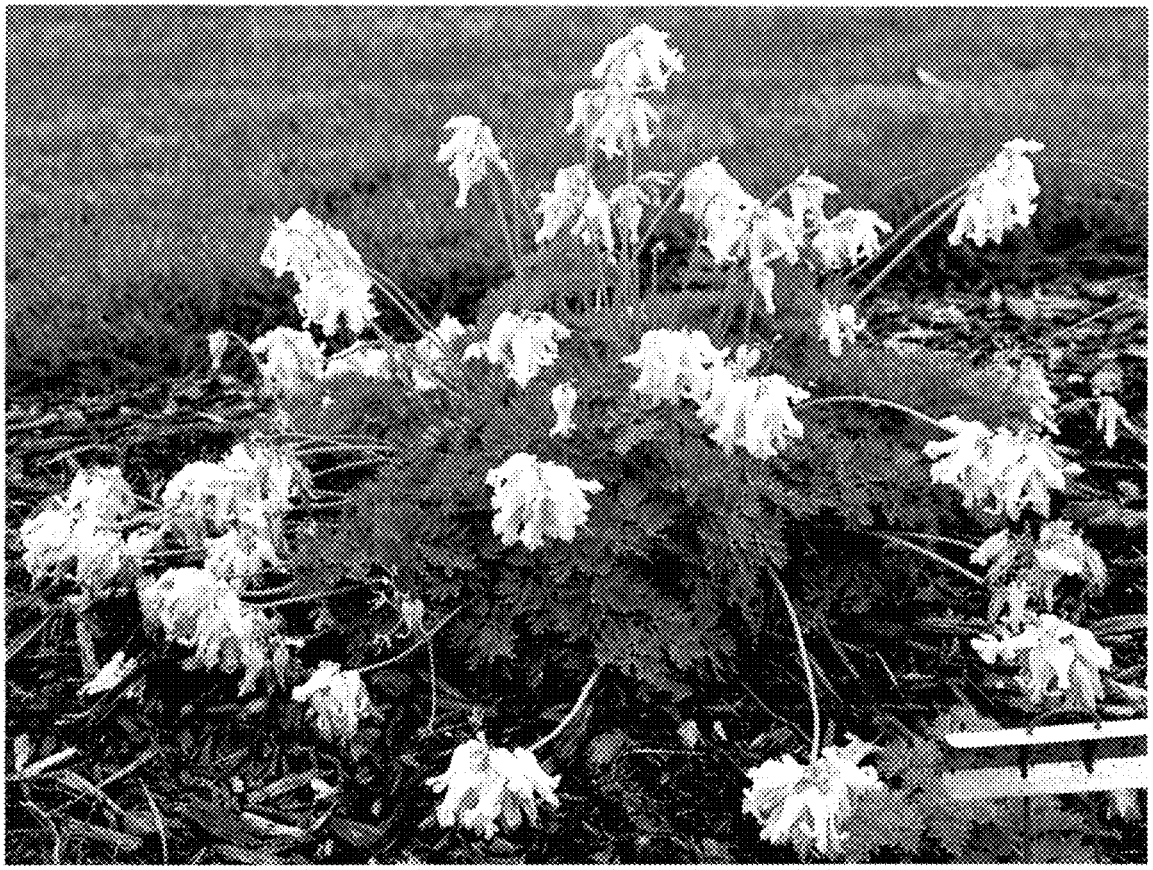
FIG. 1 shows the new plant grown in a full-sun trial garden.
Figure 2:
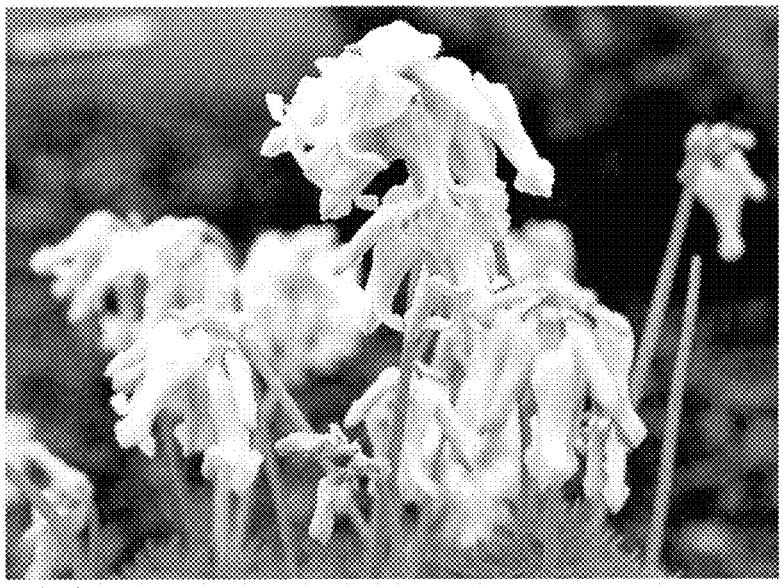
FIG. 2 shows a close-up of the flower panicle.
Figure 3:
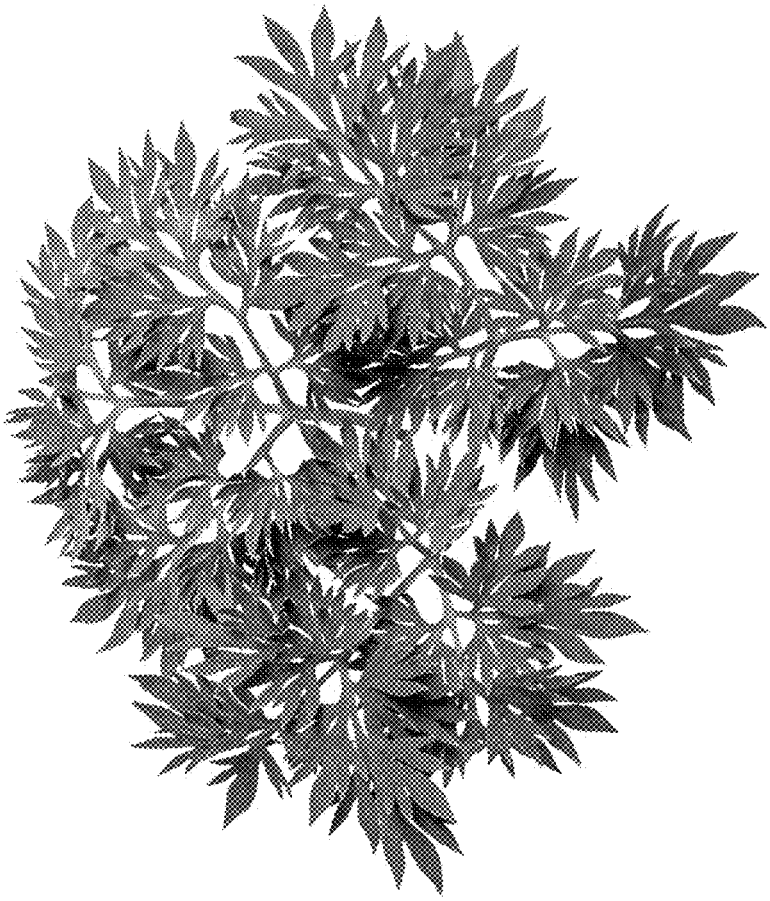
FIG. 3 shows a close-up of the foliage.

The following detailed description is based on a three-year-old plant growing in a full-sun trial garden in Zeeland, MI, USA. Environmental conditions for the growing season daytime temperatures range between 12-35° C., and night temperatures range between 6-19° C. Except for ordinary dictionary color usage, color references are according to The Royal Horticultural Society Colour Chart, 2015 edition.

Parentage: Female or seed parent is 'Ivory Hearts'; male or pollen parent is 'Red Fountain';

Asexual propagation: Plant tissue culture, time to flower from a 25 mm plug to a 3.8-liter container about 12 to 15 weeks;

Plant habit: Herbaceous, winter-hardy perennial; forming compact mound with about 20 underground divisions;

Size: Foliage grows to about 26 cm tall to top of foliage and 54 cm wide;

Vigor: Excellent; growing best in well-drained soil in full-sun;

Leaf: Triternate; dissected; deltoid in outline; to 13 cm long and 14 cm wide; glabrous adaxial and abaxial;

Lobes: To 7.5 cm long and 5.5 cm wide; each main lobe further sectioned into three with side lobes divided into three segments with up to 50 smaller divisions of lobes and terminal section divided into up to 52 divisions; secondary lobes to 3 cm wide and 3.5 cm long; individual lobes to about 8 mm across and 10 mm long; individual lobe apices acute, margin entire;

Leaf color: Emerging and developing adaxial nearest blend of RHS 189C and RHS N138D, emerging and developing abaxial nearest blend of RHS 189D and RHS N138D; mature adaxial nearest RHS N138A and RHS 189C, mature abaxial nearest RHS N138D and RHS 189C;

Venation: Pinnate;

Vein color: Same as surrounding tissue;

Petiole: Concavo-convex; flexible; to 5 cm long and 3 mm diameter above clasping base, base to about 6 mm across;

Petiole color: Nearest RHS 146C;

Inflorescence: Paniculate; to about 100 per plant; flowering in upper 9 cm to 6 cm across; between 10 to 60 flowers open at one time per stem; with new inflorescences beginning throughout flowering season;

Number of flowers: About 10 developing to up to 145 per panicle, increasing as season progresses;

Peduncle: Cylindrical; glabrous; to 39 cm long and 4 mm diameter; aspect begins upright then droops with weight of the numerous flowers; color between RHS 145A and RHS 146D;

Pedicel: Cylindrical; glabrous; slightly glaucous; to about 7 mm long and about 0.7 mm diameter; color between RHS 147C and RHS 138B;

Flower bud: One day prior to opening inverted vase-shaped, narrowest in middle; base cordate; apex acute; to about 25 mm long, 13 mm wide, 7 mm thick at the base, about 4.5 mm diameter near apex, with inflated wings extending on opposite sides of corolla to about 8 mm across; wings about 6 mm long and protruding from corolla tube about 2 mm;

Bud color: One day prior to opening proximally nearest RHS 155C; distally nearest RHS 4D; wing nearest RHS NN155C;

Flower season: Beginning week 18 and continuing for about 22 weeks;

Flower lastingness: Individually about one week; each scape about 4 to 6 weeks;

Flower: Zygomorphic; proximally cordate; laterally slightly applanate; with three sets of two petals; to about 28 mm long, 15 mm across and 7 mm thick at base, 5 mm wide at narrowest constriction, 22 mm wide at reflexed outer petal apices, 4 mm wide near inner petal apex; 8 mm wide at inflated wings;

Corolla: Two outer petals; opposite, inflated proximally, concavo-convex and reflexed distally; glabrous, fleshy and stiff; apex acute; basal 3 mm fused; margin entire; to 28 mm long extended and 8 mm across at inflated base, 5 mm wide from constriction to near apex; outer petal adaxial and abaxial color nearest RHS NN155D proximally and nearest RHS NN155C distally; inner most petals two; opposite; decussate; apex acute; base split in three or four lanceolate to linear 8 mm portions; fused in distal 17 mm; middle petal decussate to outer petal; fleshy and cupped in adaxial portion and with inflated wing in abaxial portion; apex acute with both petals fused in distal 1 mm; about 25 mm long and 5 mm wide in distal portion, 2 mm wide in basal 11 mm; with keeled, central, abaxial wing in distal 8 mm extending outwardly about 3 mm; inner most petal color adaxial and abaxial nearest RHS NN155D; middle petal color nearest RHS NN155A in adaxial cupped portion, remained of adaxial and abaxial nearest RHS NN155D;

Sepals: Two; nearly round; opposite; adpressed to corolla; apiculate apex; truncate base; margin finely serrulate; glabrous adaxial and abaxial; hyaline; to about 4.5 mm long and 4 mm wide; color nearest RHS NN155C with the center between RHS 145D and RHS 150D;

Gynoecium: Single; about 21 mm long; erect, straight;

Style: About 11 mm long and 1.0 mm diameter above ovary, tapering toward stigma; color between RHS 145C and RHS 147D;

Stigma: With a bifid apices about 0.5 mm long protruding from an applanate base about 1.5 mm across and 0.5 mm thick; color nearest base nearest RHS 143A and apices nearest RHS 4D;

Ovary: Oblong; fusiform, tapering toward style and base; apex acute; base truncate; 9 mm long and 2 mm diameter near middle; color nearest RHS 143C;

Androecium: Six; proximal one-half of filaments connate into two groups;

Filaments: Petaloid; in two groups at right angle to inner petal; fused near center 12 mm, free in distal 2 mm and basal 8 mm; two lateral and one central in each group; two lateral filaments to about 2 mm wide near base and about 22 mm long, central filament to about 1 mm wide near base and about 22 mm long, tapering to about 0.1 mm diameter in distal 2 mm; color basally nearest RHS NN155D;

Anthers: Closely arranged just below stigma; ellipsoidal; longitudinal; basifixed; about 2.5 mm long and 0.7 mm across; color nearest RHS 12A;

Pollen: Abundant; color nearest RHS 12A;

Fragrance: Lightly sweet;
Fruit and seed: No fruit or seed observed to date;
Pest and disease tolerance: 'White Diamonds' has not shown susceptibility to insects of the sub-families Aphidoidea and Aleyrodoidea or fungi of unknown scientific names that are frequent pests and diseases of other cultivars in the genus *Dicentra*.

I claim:

1. A new and distinct cultivar of Fern-leafed Bleeding Heart, *Dicentra* plant named 'White Diamonds' as herein described and illustrated.

* * * * *